United States Patent
Babij et al.

(10) Patent No.: US 10,669,237 B2
(45) Date of Patent: Jun. 2, 2020

(54) 4-((6-BROMOPYRIDIN-3-YL)OXY) BENZONITRILE AND PROCESSES OF PREPARATION

(71) Applicant: Dow AgroSciences LLC, Indianapolis, IN (US)

(72) Inventors: Nicholas R. Babij, Indianapolis, IN (US); Qiang Yang, Zionsville, IN (US); Kaitlyn Gray, Indianapolis, IN (US); Yan Hao, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 16/462,208

(22) PCT Filed: Nov. 17, 2017

(86) PCT No.: PCT/US2017/062131
§ 371 (c)(1),
(2) Date: May 17, 2019

(87) PCT Pub. No.: WO2018/094128
PCT Pub. Date: May 24, 2018

(65) Prior Publication Data
US 2019/0284139 A1   Sep. 19, 2019

Related U.S. Application Data

(60) Provisional application No. 62/423,882, filed on Nov. 18, 2016.

(51) Int. Cl.
*C07D 213/65* (2006.01)
*C07D 213/69* (2006.01)

(52) U.S. Cl.
CPC ......... *C07D 213/65* (2013.01); *C07D 213/69* (2013.01)

(58) Field of Classification Search
CPC ........................ C07D 213/65; C07D 213/69
See application file for complete search history.

(56) References Cited

U.S. PATENT DOCUMENTS

2015/0291632 A1 * 10/2015 Loso ..................... C07F 7/0812
514/63

FOREIGN PATENT DOCUMENTS

| EP | 1300396 A1 | 4/2003 |
| WO | 2014043376 A1 | 3/2014 |
| WO | 2014193974 A1 | 12/2014 |

OTHER PUBLICATIONS

International Preliminary Report of Patentability for International Application No. PCT/2017/062131, ISA/KR, dated Mar. 19, 2018, all pages.
Chemical Abstract compound, STN express. RN 179018-50-9 (Entered STN: Aug. 1, 1996).

* cited by examiner

*Primary Examiner* — Timothy R Rozof

(57) ABSTRACT

Provided herein is a process for the preparation of 4-((6-bromopyridin-3-yl)oxy)benzonitrile.

10 Claims, No Drawings

4-((6-BROMOPYRIDIN-3-YL)OXY) BENZONITRILE AND PROCESSES OF PREPARATION

CROSS-REFERENCE TO RELATED APPLICATIONS

The present application is a U.S. National Phase Patent Application based on International Application No. PCT/US2017/062131 filed Nov. 17, 2017, which claims the benefit of U.S. provisional patent application, U.S. Ser. No. 62/423,882, filed Nov. 18, 2016, the entire contents of which are incorporated herein by reference.

FIELD

Provided herein is 4-((6-bromopyridin-3-yl)oxy)benzonitrile and processes of preparation.

BACKGROUND

U.S. Patent Application Ser. No. 62/163,106 describes inter alia certain metalloenzyme inhibitor compounds and their use as fungicides. The disclosure of this application is expressly incorporated by reference herein. This patent application describes various routes to generate metalloenzyme inhibiting fungicides. It may be advantageous to provide more direct and efficient methods for the preparation of metalloenzyme inhibiting fungicides and related compounds, e.g., by the use of reagents and/or chemical intermediates which provide improved time and cost efficiency.

SUMMARY OF THE DISCLOSURE

Provided herein is the compound 4-((6-bromopyridin-3-yl)oxy)benzonitrile (I), a useful intermediate for making metalloenzyme inhibitors, and processes for its preparation. In one embodiment, provided herein, is a process for the preparation of the compound of the Formula I:

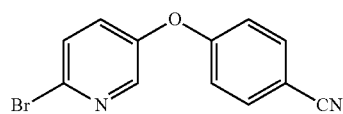

I which comprises contacting a compound of Formula II

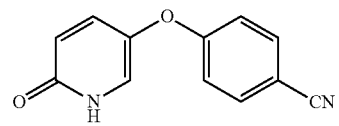

II with one or more dehydrative bromination reagents.

In another embodiment, the compound of Formula II may be prepared by contacting a compound of Formula III

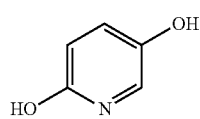

III with a compound of Formula IV

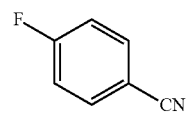

IV and a base.

Another aspect of the present disclosure is the novel intermediate produced in the present process, viz., a compound consisting of:

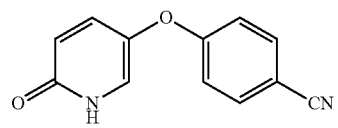 [SMILES: N#Cc1ccc(Oc2ccc(=O)[nH]c2)cc1]

The term "hydroxyl" refers to an —OH substituent.

The term "halogen" or "halo" refers to one or more halogen atoms, defined as F, Cl, Br, and I.

The term "organometallic" refers to an organic compound containing a metal, especially a compound in which a metal atom is bonded directly to a carbon atom.

Room temperature (RT) is defined herein as about 20° C. to about 25° C.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

The embodiments described above are intended merely to be exemplary, and those skilled in the art will recognize, or will be able to ascertain using no more than routine experimentation, numerous equivalents of specific processes, materials and procedures. All such equivalents are considered to be within the scope of the invention and are encompassed by the appended claims.

DETAILED DESCRIPTION 4-((6-Bromopyridin-3-yl)oxy)benzonitrile (I) is provided herein and may be prepared from 4-((6-oxo-1,6-dihydropyridin-3-yl)oxy)benzonitrile (II) as shown in Example 1.

Example 1: Preparation of 4-((6-bromopyridin-3-yl)oxy)benzonitrile (I)

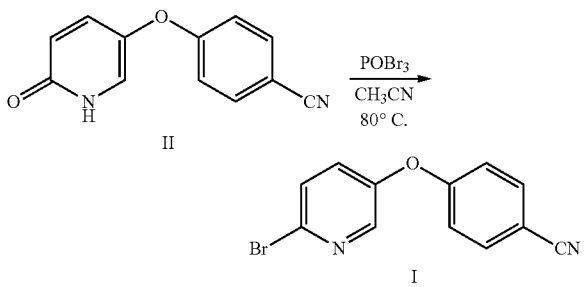

A vial was charged with phosphorus oxybromide (2.57 g, 8.95 mmol) and acetonitrile (8.9 mL) to give a clear yellow solution. 4-((6-Oxo-1,6-Dihydropyridin-3-yl)oxy)benzonitrile (II) (500 mg, 2.238 mmol) was added and the reaction was heated at 80° C. overnight. Additional phosphorus oxybromide (1.0 g, 3.49 mmol) was added and the reaction was stirred for another 3 h at 80° C. The reaction mixture was added dropwise to a flask containing about 25 mL of water cooled in an ice bath. The resulting suspension was stirred for 15 min at 0° C. resulting in a tan precipitate which was collected via vacuum filtration. The tan solid was dried overnight in a vacuum oven at 50° C. to afford 4-((6-bromopyridin-3-yl)oxy)benzonitrile (I) as a tan solid (499 mg, 1.778 mmol, 79% yield). mp: 119-122° C.; $^1$H NMR (500 MHz, CDCl$_3$) δ 8.22 (d, J=2.9 Hz, 1H), 7.71-7.61 (m, 2H), 7.54 (dd, J=8.7, 0.6 Hz, 1H), 7.33-7.24 (m, 1H), 7.15-6.99 (m, 2H). $^{13}$C NMR (126 MHz, CDCl$_3$) δ 160.1, 151.5, 142.5, 136.7, 134.5, 130.2, 129.2, 118.3, 118.3, 107.5. HRMS-ESI (m/z) [M+H]$^+$ calcd for C$_{12}$H$_7$BrN$_2$O, 274.9815; found, 274.9812.

Solvents that may be used in this process step include acetonitrile, toluene, N,N-dimethylformamide (DMF), dichloromethane (DCM), and dioxane.

Dehydrative brominating reagents that may be used in this process step include, for example, phosphorus oxybromide (POBr$_3$), phosphorus tribromide (PBr$_3$), phosphorus pentabromide (PBr$_5$), phosphorous pentoxide (P$_2$O$_5$) combined with tetrabutylammonium bromide, triphenylphosphine combined with N-bromosuccinimide, and mixtures thereof.

This process step may be conducted at temperatures from about 50° C. to about 200° C., or from about 50° C. to about 110° C.

4-((6-Oxo-1,6-dihydropyridin-3-yl)oxy)benzonitrile (II) may be prepared from pyridine-2,5-diol (III) as shown in Example 2.

Example 2: Preparation of 4-((6-oxo-1,6-dihydropyridin-3-yl)oxy)benzonitrile (II)

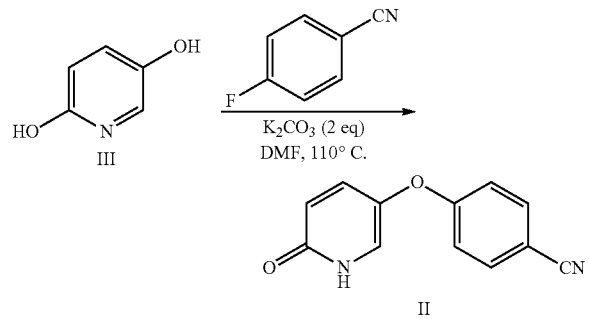

A 50 mL flask was charged with pyridine-2,5-diol (III) (2.0 g, 18.00 mmol), 4-fluorobenzonitrile (2.18 g, 18.00 mmol), potassium carbonate (4.98 g, 36.0 mmol) and DMF (25.7 mL). The reaction was heated at 110° C. overnight, and then allowed to cool to room temperature. The reaction was quenched with water (50 mL) and diluted with ethyl acetate. The layers were separated and the aqueous layer was extracted with ethyl acetate. The combined organic layers were washed with brine (3×). The organic layer was then dried over anhydrous sodium sulfate, filtered, and concentrated. DCM was added resulting in a brown precipitate which was collected via vacuum filtration. The wetcake was dried to give 4-((6-oxo-1,6-dihydropyridin-3-yl)oxy)benzonitrile (II) as a tan solid (2 g, 8.95 mmol, 49.7% yield). mp: 223-226° C. $^1$H NMR (500 MHz, DMSO-d$_6$) δ 11.66 (s, 1H), 7.86-7.76 (m, 2H), 7.57 (d, J=3.2 Hz, 1H), 7.43 (dd, J=9.7, 3.2 Hz, 1H), 7.20-6.99 (m, 2H), 6.49 (d, J=9.7 Hz, 1H). $^{13}$C NMR (126 MHz, DMSO-d$_6$) δ 162.3, 161.7, 137.1, 136.9, 135.0, 129.8, 120.2, 119.2, 117.2, 105.2. HRMS-ESI (m/z) [M+H]$^+$ calcd for C$_{12}$H$_8$N$_2$O$_2$, 213.0659; found, 213.0653.

Bases that may be used in this process step include, for example, potassium carbonate, cesium carbonate, sodium carbonate, sodium hydride, potassium hydride, sodium hydroxide, and potassium hydroxide.

Suitable solvents for use in this process step may be selected from at least one of dimethylsulfoxide (DMSO), N,N-dimethylformamide (DMF), N,N-dimethylacetamide (DMA), sulfolane, and N-methyl-2-pyrrolidone (NMP).

This process step may be conducted at temperatures from about 50° C. to about 200° C., or from about 80° C. to about 120° C.

What is claimed is:

1. A method of making a compound of Formula I

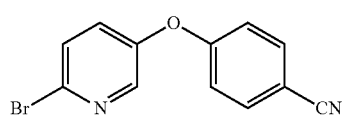

comprising the step of contacting a compound of Formula II

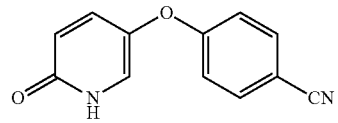 [SMILES: N#Cc1ccc(Oc2ccc(=O)[nH]c2)cc1]

with a dehydrative brominating reagent.

2. The method of claim 1, further comprising a solvent selected from the group including acetonitrile, toluene, DMF, DCM, and dioxane.

3. The method of claim 1 wherein the dehydrative brominating reagent may be selected from the group including POBr$_3$, PBr$_3$, PBr$_5$, P$_2$O$_5$ combined with tetrabutylammonium bromide, triphenylphosphine combined with N-bromosuccinimide, and mixtures thereof.

4. The method of claim 1 wherein the dehydrative brominating reagent may be selected from POBr$_3$, PBr$_5$, and mixtures thereof.

5. The method of claim 1, wherein the contacting is carried out between about 50° C. and about 200° C.

6. The method of claim 1, further comprising the step of: contacting a compound of Formula III

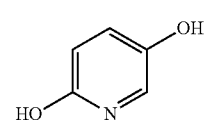

with a compound of Formula IV and a base

IV to prepare the compound of Formula II.

7. The method of claim 6 wherein the base is selected from the group including cesium carbonate, potassium carbonate, sodium hydride, potassium hydride, sodium hydroxide, and potassium hydroxide.

8. The method of claim 6 further comprising a solvent selected from the group including dimethylsulfoxide, N,N-dimethylacetamide, N,N-dimethylformamide, sulfolane, and N-methyl-2-pyrrolidone.

9. The method of claim 6 wherein the contacting is carried out between about 50° C. and about 200° C.

10. A compound consisting of:

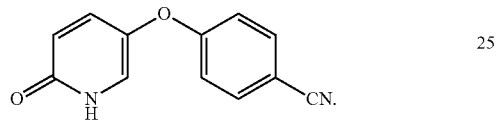

* * * * *